(12) United States Patent
Cheung

(10) Patent No.: US 10,544,421 B1
(45) Date of Patent: Jan. 28, 2020

(54) SYSTEM AND METHOD FOR CREATING CRYSTALS OF HUMAN ACETYLCHOLINESTERASE WITH OPEN ACTIVE SITES

(71) Applicant: New York Structural Biology Center, New York, NY (US)

(72) Inventor: Jonah Cheung, Brooklyn, NY (US)

(73) Assignee: New York Structural Biology Center, New York, NY (US)

( * ) Notice: Subject to any disclaimer, the term of this patent is extended or adjusted under 35 U.S.C. 154(b) by 0 days.

(21) Appl. No.: 15/469,227

(22) Filed: Mar. 24, 2017

Related U.S. Application Data

(63) Continuation-in-part of application No. 13/921,572, filed on Jun. 19, 2013, now abandoned.

(60) Provisional application No. 61/661,432, filed on Jun. 19, 2012.

(51) Int. Cl.
| | |
|---|---|
| C12N 9/18 | (2006.01) |
| C12N 15/66 | (2006.01) |
| C12N 15/10 | (2006.01) |
| C12N 9/64 | (2006.01) |
| C07K 14/47 | (2006.01) |

(52) U.S. Cl.
CPC .............. *C12N 15/66* (2013.01); *C07K 14/47* (2013.01); *C12N 9/6421* (2013.01); *C12N 15/1031* (2013.01)

(58) Field of Classification Search
None
See application file for complete search history.

(56) References Cited

PUBLICATIONS

Cheung et al., "Supporting Information" for "Structures of human acetylcholinesterase in complex with pharmacologically important ligands", 7 pages, 2012, obtained from pubs.acs.org/doi/suppl/10.1021/jm300871x.*
pcDNA™ 3.3-TOPO® TA Cloning Kit User Guide, May 2011.*
GenBank Accession No. BC105062, Jun. 2006, 2 pages.*
Dvir et al., "Acetylcholinesterase: From 3D Structure to Function", 187 Chemico-Biological Interactions, pp. 10-22 (2010).
Wiencek, "New Strategies for Protein Crystal Growth", 01 Annu. Rev. Biomed. Eng., pp. 505-534 (1999).
Mallender et al., "Organophosphorylation of Acetylcholinesterase in the Presence of Peripheral Site Ligands", 274 J. Biol. Chem., pp. 8491-8499 (1999).
Kronman et al."Prod. & Secr. High Levels of Recombinant Human Acetylcholinesterase in Cultured Cell Lines:Microheterogeneity of the Catalytic Subunit",121(2)Gene 295-304 (1992).
Kuhn et al., "The Baculovirus Expression Vector pBSV-8His Directs Secretion of Histidine-Tagged Proteins", 162 Gene pp. 225-229 (1995).
Hyvonen, "Guide to Expression Construct Cloning", http://camelot.bioc.cam.ac.uk/~marko/methods/cloning.pdf (2004).
Nemetz et al., "RTS:Rapid Protein Expression Directly from PCR Fragment", Biochemica No. 2, www.Roche-Applied-Science.com (2002).

* cited by examiner

*Primary Examiner* — David Steadman
(74) *Attorney, Agent, or Firm* — LaMorte & Associates, P.C.

(57) ABSTRACT

A system and method for creating crystals from human acetylcholinesterase. The crystals can then be analyzed using X-ray crystallography. A segment of DNA for human acetylcholinesterase is isolated that includes the codon sequence GAGGGC. A polyhistidine tag is inserted between codon GAG and codon GGC to produce a recombinant acetylcholinesterase construct. The recombinant acetylcholinesterase construct is used to transfect cells on a prepared growth medium. The growing cells secrete a portion of the recombinant acetylcholinesterase construct. The secreted portion is concentrated and the tag cleaved. The concentrate is then buffered and used to form crystals.

Figure 1:
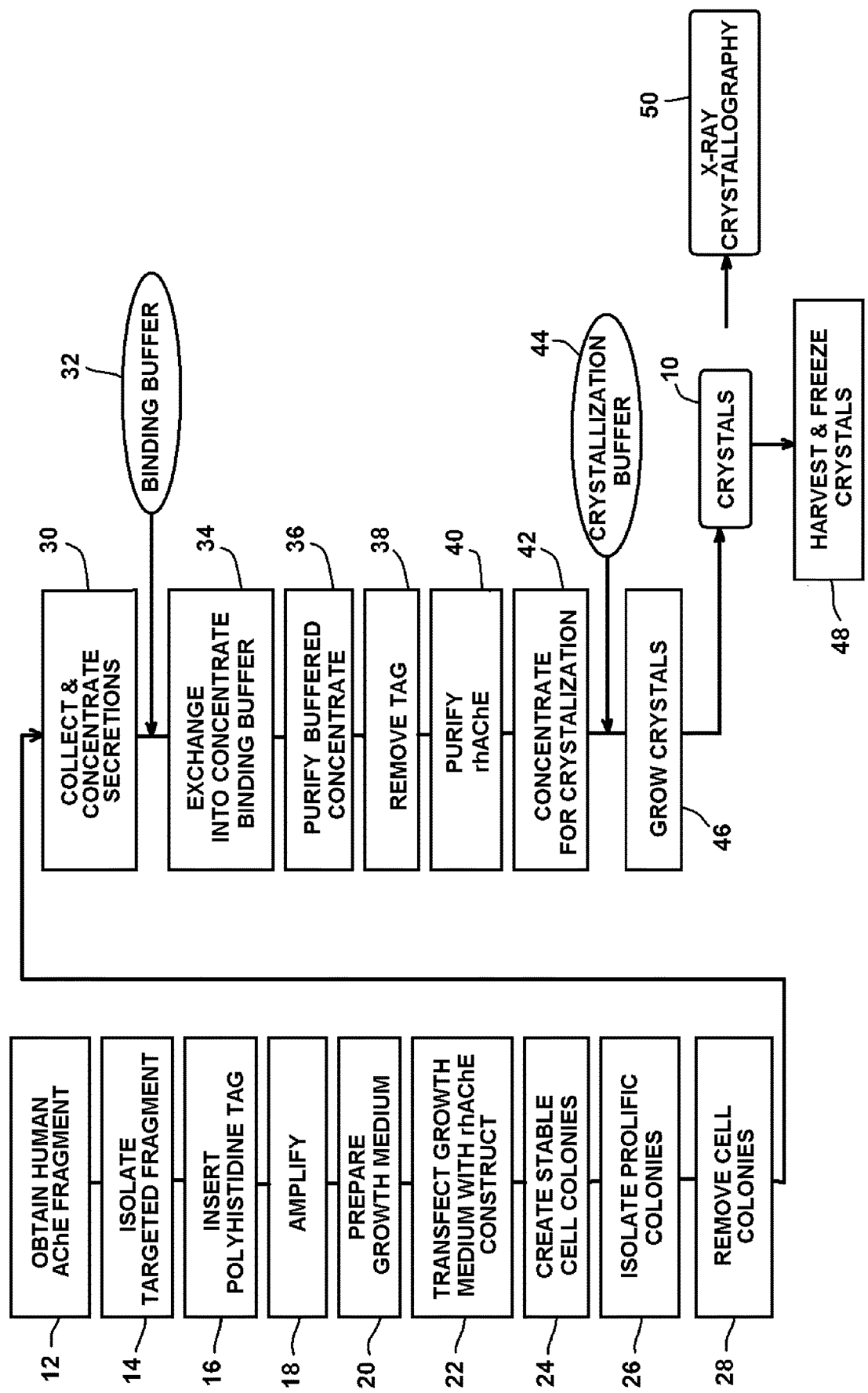

12 Claims, 3 Drawing Sheets
Specification includes a Sequence Listing.

SEQUENCE LISTING

```
<160> NUMBER OF SEQ ID NOS: 3

<210> SEQ ID NO 1
<211> LENGTH: 6
<212> TYPE: PRT
<213> ORGANISM: tobacco Etch Virus
<300> PUBLICATION INFORMATION:
<308> DATABASE ACCESSION NUMBER: Merops c04.04
<309> DATABASE ENTRY DATE: 2000-12-04
<313> RELEVANT RESIDUES IN SEQ ID NO: (1)..(6)

<400> SEQUENCE: 1

Glu Asn Leu Tyr Phe Gln
1               5

<210> SEQ ID NO 2
<211> LENGTH: 11
<212> TYPE: DNA
<213> ORGANISM: human
<300> PUBLICATION INFORMATION:
<308> DATABASE ACCESSION NUMBER: GenBank: BC105060.1
<309> DATABASE ENTRY DATE: 2006-07-21
<313> RELEVANT RESIDUES IN SEQ ID NO: (32)..(35)

<400> SEQUENCE: 2
gagggccggg a                                                          11

<210> SEQ ID NO 3
<211> LENGTH: 8
<212> TYPE: DNA
<213> ORGANISM: human
<300> PUBLICATION INFORMATION:
<308> DATABASE ACCESSION NUMBER: GenBank: BC105060.1
<309> DATABASE ENTRY DATE: 2006-07-21
<313> RELEVANT RESIDUES IN SEQ ID NO: (33)..(35)

<400> SEQUENCE: 3 ggccggga                                                               8
```

SYSTEM AND METHOD FOR CREATING CRYSTALS OF HUMAN ACETYLCHOLINESTERASE WITH OPEN ACTIVE SITES

RELATED APPLICATIONS

This application is a continuation-in-part of co-pending U.S. application Ser. No. 13/921,572, filed Jun. 19, 2013, now abandoned, which claims the benefits of provisional patent application No. 61/661,432, filed Jun. 19, 2012.

GOVERNMENT RIGHTS STATEMENT

This invention was made with Government support under grant numbers W911SR-11-C-0014 and W911SR-12-C-0006 awarded by the United States Department of Defense. The United States Government has certain rights in the invention.

BACKGROUND OF THE INVENTION

1. Field of the Invention

In general, the present invention relates to the creation of crystals from acetylcholinesterase and to systems that utilize such crystals to produce digital models through X-ray crystallography. More particularly, the present invention relates to the methodology of creating crystals from human acetylcholinesterase.

2. Prior Art Description

Acetylcholinesterase, also known as AChE is a serine protease that hydrolyzes the neurotransmitter acetylcholine (ACh). AChE is found at mainly neuromuscular junctions and cholinergic brain synapses, where it serves to terminate synaptic transmission. For a cholinergic neuron to receive another impulse, ACh must be released from the ACh receptor. This occurs only when the concentration of ACh in the synaptic cleft is very low.

During neurotransmission, ACh is released from the nerve into the synaptic cleft and binds to ACh receptors on the post-synaptic membrane, relaying the signal from the nerve. AChE, which is also located on the post-synaptic membrane, terminates the signal transmission by hydrolyzing the ACh, therein liberating a choline. The liberated choline is taken up again by the pre-synaptic nerve and ACh is synthesized by combining with acetyl-CoA through the action of choline acetyltransferase.

Inhibition of AChE leads to accumulation of ACh in the synaptic cleft. This results in impeded neurotransmission or a cessation of neurotransmission. Consequently, inhibition of AChE may lead to muscular paralysis, convulsions, bronchial constriction, and death by asphyxiation. As a result, inhibitors of AChE have proven to be very effective nerve toxins and insecticides.

Substances that inhibit AChE also have useful medical applications and are used to treat various neurological diseases. For example, Alzheimer's disease is a disease that affects cholinergic neurotransmission. Cholinesterase inhibitor drugs, such as donepezil, galantamine, rivastigmine, and huperzine A, have been extensively studied as symptomatic treatments for Alzheimer's disease.

In order to effectively study the effects of any compound that reacts with human AChE, human AChE must first be accurately modeled. The way that AChE is modeled first entails forming crystals of AChE. The crystals are then subjected to X-ray crystallography. X-ray crystallography is a method used for determining the atomic and molecular structure of a crystal, whereby the crystalline atoms cause a beam of X-rays to diffract into many specific directions. By measuring the angles and intensities of these diffracted beams, a crystallographer can produce a three-dimensional model of the density of electrons within the crystal. From this electron density map, the mean positions of the atoms in the crystal can be determined, as well as their chemical bonds, any disorder among atoms, and various other information that can be used to create an accurate digital model.

In the prior art, models of AChE have been derived from crystals of material taken from various animals, such as the electric ray (*Torpedo californica*). Such prior art is exemplified by the publication Chemico-Biological Interactions (2010 Feb. 4) 187, 10-22, by Dvir and the publication Ann. Rev. Biomed. Eng. 1999, 1, 505-534 by Wiencek. However, there are significant differences between human AChE and AChE from lesser animals. These differences result in inaccurate and ineffective models for use in testing nuanced drugs. The Applicant and previous researchers have determined through chemical analysis and biochemical methods that there are active sites on human AChE that play particularly important roles when human AChE reacts with compounds that are AChE inhibitors. One of the more active sites is physically located in the bottom of a depression on the human AChE molecule, that the Applicant calls an active site gorge. In order to accurately model a human AChE, this active site gorge must not be blocked or otherwise compromised as the human AChE is processed into crystals.

Attempts have been made to produce crystals from human AChE. However, such attempts typically required the use of snake venom fasciculin-2, which binds to the AChE. The snake venom binds to the AChE in such a manner that it partially blocks the active site gorge on the human AChE molecule and/or causes molecules of human AChE to combine in orientations that partially block the active gorge site. Binding with snake venom may also distort the AChE molecule. This changes the structure of the AChE molecule and compromises its biological relevance when studying the binding of inhibitors. This makes the resulting crystal ineffective in testing compounds that may react with active sites.

A need therefore exists for a system and method for creating better crystals of human AChE wherein active gorge sites remain unblocked, therein resulting in better modeling of the protein via X-ray crystallography. This need is met by the present invention as described and claimed below.

SUMMARY OF THE INVENTION

The present invention sets forth a system and method for creating crystals from human acetylcholinesterase. The crystals can then be analyzed using X-ray crystallography to obtain a better model of human acetylcholinesterase.

To produce the crystals, a codon sequence is isolated from a human DNA fragment that encodes for human acetylcholinesterase. The codon sequence has an initiation codon that begins the codon sequence, and a stop codon that ends the codon sequence. The codon sequence includes a GAG codon at the $32^{nd}$ codon position and a GGC codon at the $33^{rd}$ codon position, as counted from the starting position of the initiation codon.

A polyhistidine tag is inserted into the sequence between the GAG codon and the GGC codon, therein forming a recombinant acetylcholinesterase construct. The recombinant acetylcholinesterase construct is amplified. The amplified recombinant acetylcholinesterase construct is used to transfect cells on a prepared growth medium. A colony of cells is generated as the transfected cells grow. The colony of cell secretes a portion of the recombinant acetylcholinesterase construct into the growth medium. The portion secreted includes the polyhistidine tag and part of the codon segment between the 33$^{rd}$ codon and the stop codon.

The secreted portion of the recombinant acetylcholinesterase construct is separated from said growth medium to form a concentrate. The polyhistidine tag is cleaved to remove the polyhistidine tag from the concentrate. The concentrate is then purified. The purified concentrate is exchanged into a buffer to create a buffered concentrate. The buffered concentrate is used to grow crystals using sitting drop vapor diffusion.

BRIEF DESCRIPTION OF THE DRAWINGS

For a better understanding of the present invention, reference is made to the following description of an exemplary embodiment thereof, considered in conjunction with the accompanying drawings, in which:

FIG. 1 is a block logic-flow diagram that illustrates the methodology of the present invention;

FIG. 2 shows a representation of a codon sequence that encodes for human AChE that is contained within Seq. No. 1 of the sequence listings;

FIG. 3 shows a representation of the recombinant AChE construct created from the codon sequence of FIG. 2; and FIG. 4 is a block logic-flow diagram that illustrates additional steps used in making a crystal complexed with a ligand.

DETAILED DESCRIPTION OF THE DRAWINGS

The methodologies used to produce crystals that are explained below are exemplary. The methodologies can be varied using undescribed, yet functionally equivalent method steps. The methodologies described set forth some of the best embodiments contemplated for the invention. The methodologies, however, are merely exemplary and should not be considered limitations to the novelty of the invention as described and claimed.

Referring to FIG. 1, the creation of a base rhAChE crystal 10 is described. The rhAChE crystal 10 is a protein crystal. The base rhAChE crystal 10 is not complexed with a ligand or compromised with a secondary compound, such as snake venom. Consequently, the rhAChE crystal 10 contains active sites that are not blocked or partially blocked by secondary compounds. The result is an rhAChE crystal 10 of higher quality than has been fabricated before in the art. Models created from the rhAChE crystal 10, therefore, better represent AChE as it naturally appears in the human brain and peripheral nervous system.

The process begins with obtaining a cloned DNA fragment (cDNA) that contains the gene sequence that codes for human acetylcholinesterase. The cDNA is obtained from a commercial source. See Block 12. One such commercial source is clone sequence BC105060.1 (I.M.A.G.E. 8144063) sold by the Invitogen division of Thermo Fisher Scientific (Waltham, Mass.). The cDNA fragment is shipped in its accompanying plasmid. The plasmid is removed using standard DNA fragment preparation protocols.

The cDNA fragment represented in Table 1 contains approximately 1966 bases in its sequence. See Table 1 provided below. Table 1 shows the listed I.M.A.G.E. 8144063 base sequence that contains the encoding sequence for human AChE. Table 1 corresponds to Seq. No. 1 in the corresponding sequence listings.

TABLE 1

| | | | | | | |
|---|---|---|---|---|---|---|
| 1 | gaacatcggc | cgcctccagc | tcccggcgcg | gcccggcccg | gcccggctcg | gccgcctcag |
| 61 | cagacgccgc | ctgccctgca | gccatgaggc | ccccgcagtg | tctgctgcac | acgccttccc |
| 121 | tggcttcccc | actccttctc | ctcctcctct | ggctcctggg | tggaggagtg | gggctgagg |
| 181 | gccgggagga | tgcagagctg | ctggtgacgg | tgcgtggggg | ccggctgcgg | ggcattcgcc |
| 241 | tgaagacccc | cgggggccct | gtctctgctt | tcctgggcat | ccccttgcg | gagccaccca |
| 301 | tgggaccccg | tcgctttctg | ccaccggagc | ccaagcagcc | ttggtcaggg | gtggtagacg |
| 361 | ctacaacctt | ccagagtgtc | tgctaccaat | atgtggacac | cctataccca | ggttttgagg |
| 421 | gcaccgagat | gtggaacccc | aaccgtgagc | tgagcgagga | ctgcctgtac | ctcaacgtgt |
| 481 | ggacaccata | cccccggcct | acatccccca | cccctgtcct | cgtctggatc | tatgggggtg |
| 541 | gcttctacag | tggggcctcc | tccttggacg | tgtacgatgg | ccgcttcttg | gtacaggccg |
| 601 | agaggactgt | gctggtgtcc | atgaactacc | gggtgggagc | ctttggcttc | ctggccctgc |
| 661 | cggggagccg | agaggccccg | ggcaatgtgg | gtctcctgga | tcagaggctg | gccctgcagt |
| 721 | gggtgcagga | gaacgtggca | gccttcgggg | gtgacccgac | atcagtgacg | ctgtttgggg |
| 781 | agagcgcggg | agccgcctcg | gtgggcatgc | acctgctgtc | cccgcccagc | cggggcctgt |
| 841 | tccacagggc | cgtgctgcag | agcggtgccc | ccaatggacc | ctgggccacg | gtgggcatgg |
| 901 | gagaggcccg | tcgcagggcc | acgcagctgg | cccaccttgt | gggctgtcct | ccaggcggca |
| 961 | ctggtgggaa | tgacacagag | ctggtagcct | gccttcggac | acgaccagcg | caggtcctgg |
| 1021 | tgaaccacga | atggcacgtg | ctgcctcaag | aaagcgtctt | ccggttctcc | ttcgtgcctg |

TABLE 1-continued

```
1081 tggtagatgg agacttcctc agtgacaccc cagaggccct catcaacgcg ggagacttcc 1141 acggcctgca ggtgctggtg ggtgtggtga aggatgaggg ctcgtatttt ctggtttacg 1201 gggcccagg cttcagcaaa gacaacgagt ctctcatcag ccgggccgag ttcctggccg 1261 gggtgcgggt cggggttccc caggtaagtg acctggcagc cgaggctgtg gtcctgcatt 1321 acacagactg gctgcatccc gaggaccccgg cacgcctgag ggaggccctg agcgatgtgg 1381 tgggcgacca caatgtcgtg tgccccgtgg cccagctggc tgggcgactg gctgcccagg 1441 gtgcccgggt ctacgcctac gtctttgaac accgtgcttc cacgctctcc tggcccctgt 1501 ggatgggggt gccccacggc tacgagatcg agttcatctt tgggatcccc ctggaccct 1561 ctcgaaacta cacggcagag gagaaaatct tcgcccagcg actgatgcga tactgggcca 1621 actttgcccg cacaggggat cccaatgagc cccgagaccc caaggcccca caatggcccc 1681 cgtacacggc gggggctcag cagtacgtta gtctggacct gcggccgctg gaggtgcggc 1741 gggggctgcg cgcccaggcc tgcgccttct ggaaccgctt cctccccaaa ttgctcagcg 1801 ccaccgcctc ggaggctccc agcacctgcc caggcttcac ccatggggag gctgctccga 1861 ggcccggcct cccctgccc ctcctcctcc tccaccagct tctcctcctc ttcctctccc 1921 acctccggcg gctgtgaaca cggcctcttc ccctacggcc acaggg
```

Figure 2:
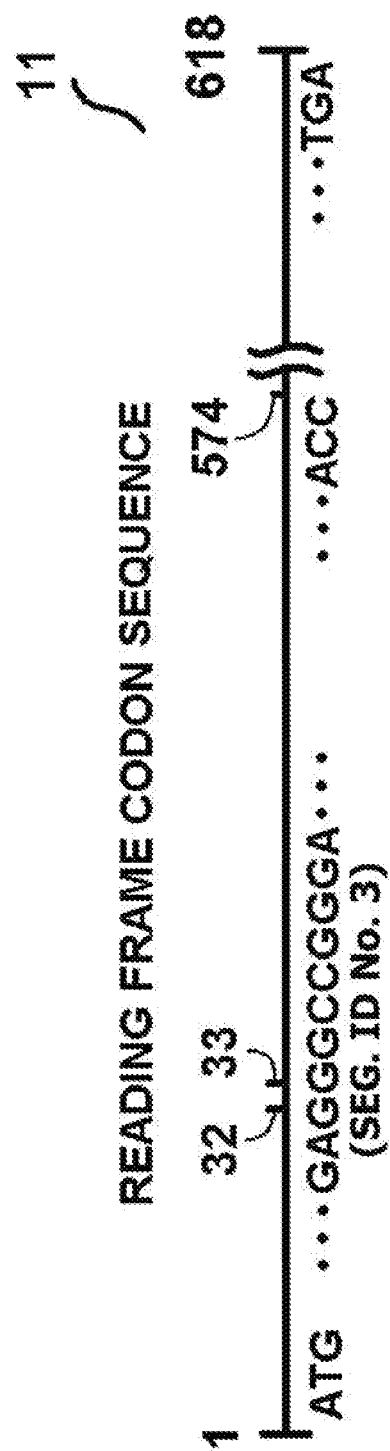

The frame of the listed base sequences that actually codes for human AChE is contained within an open reading frame that begins at position 84 and ends at position 1937 of Table 1. The open reading frame begins at table position 84 with initiation codon ATG and ends at table position 1937 with stop codon TGA. It will therefore be understood that the open reading frame that encodes for human AChE is a sequence of 1854 bases. The open reading frame of 1854 bases contains 618 codons, wherein each sequential three-base combination is a codon that encodes for an amino acid in the human AChE protein with the exception of the last stop codon. The stop codon TGA directs the termination of translation of DNA to protein at that site and does not encode an amino acid. The open reading frame begins with initiation codon ATG and ends with stop codon TGA. The open reading frame codon sequence 11 is shown in FIG. 2. The reading frame codon sequence 11 of FIG. 2 is a static feature specific to the human AChE protein, and not to the cloned DNA of Table 1. Cloned DNA from different sources may have different extraneous sections, however, the reading frame codon sequence 11 should remain a constant.

Referring to FIG. 2 in conjunction with FIG. 1, it will be understood that the reading frame codon sequence 11 is a sequence of 618 codons that begin at initiation codon ATG and end at stop codon TGA. In FIG. 2, the codons within the reading frame codon sequence 11 are numbered from 1 to 618 wherein the first codon is the initiation codon ATG. This first codon corresponds to base positions 84, 85 and 86 in Table 1 and in different positions in cloned DNA from other sources.

A targeted segment of the reading frame codon sequence 11 is first isolated using conventional molecular biology techniques. Using pre-processed protein 5 numbering, including native secretion signal, a the segment of the human DNA fragment 11 to be isolated extends from the initiation codon ATG to a targeted codon. The targeted codon is the 574th codon ACC. The targeted codon ACC ends at base position 1805 in Table 1. See Block 14.

Accordingly, in the isolated segment of the reading frame codon sequence 11 starts with the initiation codon ATG at codon position No. 1 and extends a to new TGA stop codon that is added to codon position 575 after the ACC codon at position 574.

Figure 3:
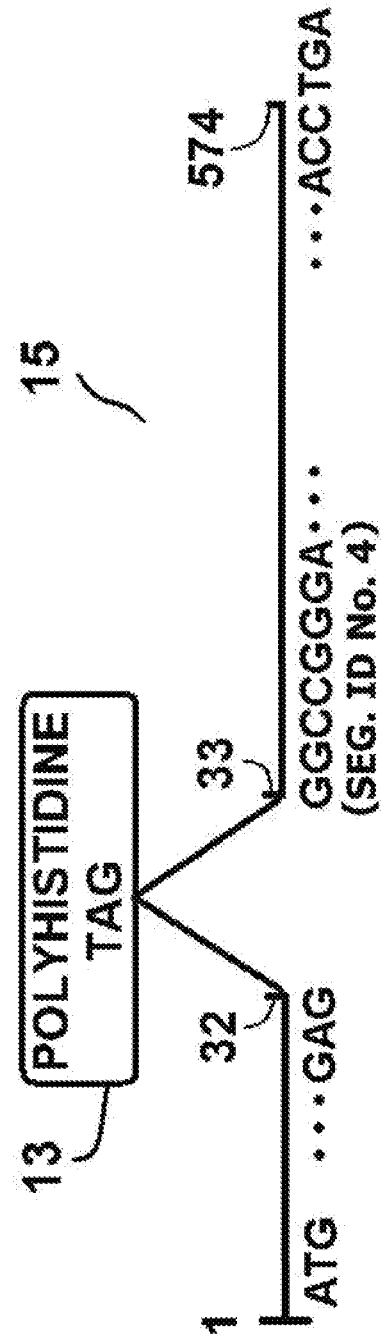

Referring to FIG. 3 in conjunction with FIG. 1 and FIG. 2, it will be understood that a polyhistidine tag 13 is added to the isolated segment of the reading frame codon sequence 11. See Block 16. The polyhistidine tag 12 is an octahistidine tag followed by the protease recognition sequence ENLYFQ (SEQ. ID No. 2). The polyhistidine tag 12 is inserted between codon GAG and codon GGC, which corresponds to between codon 32 and codon 33 on the reading frame codon sequence 11. As is indicated in FIG. 2 and FIG. 3, the insertion point is contained within the base sequence fragment GAGGGCCGGGA (SEQ. ID No. 3) wherein the polyhistidine tag 12 is added between codon GAG and codon GGC. This forms a recombinant human acetylcholinesterase (rhAChE) construct 15 of FIG. 3. The rhAChE construct 15 contains a complete TEV-10 protease site of ENLYFQ (SEQ. ID No. 2) with the addition of a C-terminal glycine.

The rhAChE construct 15 is amplified using polymerase chain reaction (PCR) protocols. See Block 18. The rhAChE construct 15 is amplified using the appropriate primers. The amplified rhAChE construct 15 is then cloned in the appropriate plasmid vectors and reagents, such as those provided in the pcDNA™ 3.3-TOPO® brand cloning kit sold by Invitrogen division of Thermo Fischer Scientific (Waltham, Mass.).

A growth medium is prepared by growing an adherent layer of human embryonic kidney cells (HEK 293-H cells) in a basal medium, such as the DMEM GlutaMAX medium sold by Thermo Fischer Scientific (Waltham, Mass.). See Block 20. The basal medium preferably contains 10% heat-inactivated fetal bovine serum. Once the HEK 293-H cells have matured, the HEK 293-H cells are co-transfected with approximately 0.8 µg each of the amplified rhAChE construct 15 and an appropriate plasmid, such as the integrase-expressing plasmid pJTI PhiC31 Int, sold by the Invitogen division of Thermo Fisher Scientific (Waltham, Mass.). See Block 22. Using a transfection reagent, such as Lipofectamine®, with growth media containing a protein synthesis inhibitor, such as 150 µg/L Hygromycin-B®, growth is promoted for approximately 10 days. This creates stable colonies of cells. See Block 24.

After growth is stabilized, individual cell colonies are isolated by dilution of cells from the stable pool into 96-well plates. Growth is subsequently expanded in the well plates. Relative expression levels are determined once the expansion of the cell colonies reaches the 6-well level on the well plates. The expression levels are determined using an appropriate assay kit, such as the QuantiChrom Acetylcholinesterase Assay Kit from BioAssay Systems (Hayward, Calif.). The most prolific of the cell colonies are selected for expansion into cell culture vessels. See Block 26. As the selected prolific cell colonies grow, they secrete a portion of the recombinant rhAChE with the octahistidine tag into the cell growth media. That is, the cell colonies secrete the segment of the recombinant rhAChE from the polyhistidine tag to stop codon ACC at after codon 574. The fragment in the construct between the initiation codon ATG and the polyhistidine tag are used to direct the secretion. After secretion, the cell colonies are removed from the growth medium and can be preserved for future use. See Block 28.

What remains is the cell growth medium that contains the secreted octahistidine-tagged recombinant rhAChE. The tagged recombinant rhAChE is separated from the cell growth media. The removed tagged recombinant rhAChE is then concentrated. See Block 30. A binding buffer 32 is provided. The preferred binding buffer 32 contains 20 mM 4-(2-hydroxyethyl)piperazine-1-ethanesulfonic acid (HEPES) pH 7.6, 500 mM NaCl, and 40 mM imidazole. The tagged recombinant rhAChE concentrate is then exchanged into the binding buffer 32 using cross-flow diafiltration cells. See Block 34. A two-column purification system is utilized to purify the tagged recombinant rhAChE from the buffered concentrate. The two-column purification system includes a 1 mL nickel affinity column followed by gel filtration column, such as the Superdex 200 16/20 gel filtration column, sold by GE Healthcare Bio-Sciences (Pittsburgh, Pa.). See Block 36. The elution buffer consists of 0.5M imidazole in binding buffer, and the gel filtration buffer consists of 20 mM HEPES pH 7.6, 150 mM NaCl, and 20 mM imidazole.

After purification, the polyhistidine tag 16 is cleaved from the tagged recombinant rhAChE, leaving just the desired cleaved protein of rhAChE. The tagged recombinant rhAChE is pooled and the tag cleaved using a his-TEV protease. See Block 38. This process takes approximately four hours at room temperature. With the polyhistidine tag removed, the remaining cleaved protein corresponds to human acetylcholinesterase fragment from codon 33 to codon 574 as shown in FIG. 2 and FIG. 3. The cleaved rhAChE is passed over a 1 mL Ni-NTA agarose gravity column to remove the his-TEV protease, any cleaved tag residues, and any residual un-cleaved proteins. See Block 40. This produces a purified rhAChE.

The purified rhAChE is dialyzed overnight into a storage buffer, such as 10 mM HEPES (pH 7.0) and 10 mM NaCl. The solution is concentrated to 16-20 mg/ml for crystallization. See Block 42.

A crystallization buffer 44 is provided. The preferred crystallization buffer 44 contains 15-21% polyethylene glycol (PEG) 3350 and 0.17-0.21M potassium nitrate. Crystals of rhAChE are grown by sitting drop vapor diffusion at 22° C. against the crystallization buffer 44. See Block 46. Clustered hexagonal rod-shaped crystals (20×20×600 µm) are typically nucleated within 5 days and grow to full size within 3 days. Once the crystals are full size, they are harvested and flash frozen using liquid nitrogen. See Block 48. The harvested crystals 10 can then be cut and subjected to X-ray crystallography and modeling in the traditional manner. See Block 50. Since the rhAChE crystals 10 are not complexed, the X-ray crystallography produces models that more accurately represent AChE in the human brain. Additionally, the active sites that are obfuscated by snake venom in the prior art are open and active.

For the purposes of experimentation and/or comparison, it may be desirable to produce rhAChE crystals that are intentionally complexed with small molecular ligands. This may be done to model how certain drugs interact with AChE on the molecular level. The complexed rhAChE crystals can be produced using two methodologies.

Figure 4:
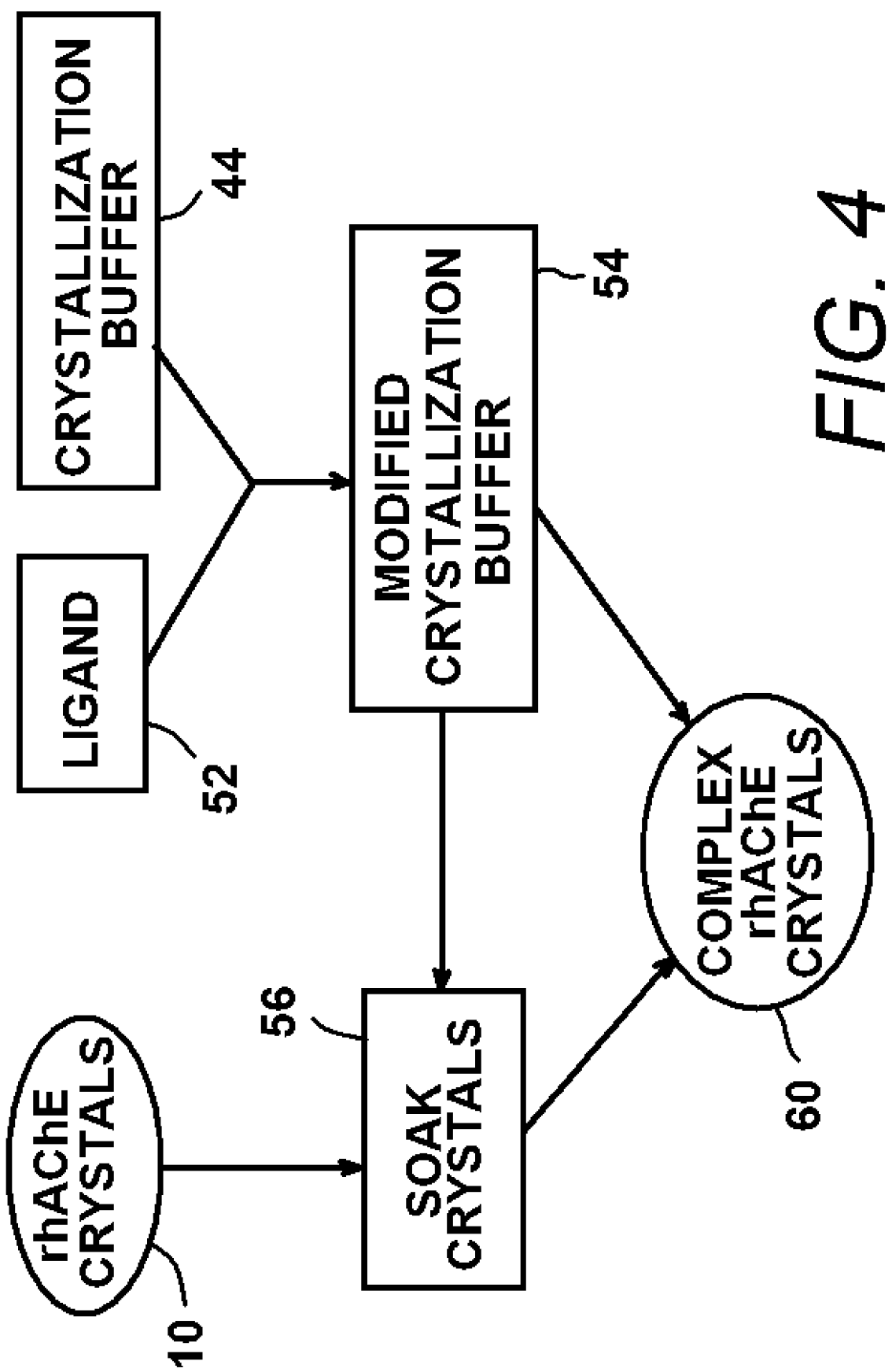

Referring to FIG. 4 in conjunction with FIG. 1, it will be understood that in order to complex the rhAChE crystals 10, a small volume of the complexing ligand 52 is added to the crystallization buffer 44 to create a modified crystallization buffer 54. Crystals of complexed rhAChE are grown by sitting drop vapor diffusion against the modified crystallization buffer 54. The crystals are then grown, harvested and imaged in the manner previously described.

Base rhAChE crystals 10 are produced using the methodology previously described. The resulting rhAChE crystals 10 are grown and harvested. A modified crystallization buffer 54 is then created by mixing the complexing ligand 52 into the crystallization buffer 44. The rhAChE crystals 10 are then soaked in a modified crystallization buffer 54. See Block 56.

After the soak, the new complex crystals 60 are produced. The complex crystals 60 are flash frozen, cut, and subjected to X-ray crystallography in the manner previously described.

The compound used as the ligand 52 can include, without limitation, any chemical compound that has an affinity to the active site of human AChE. For example, the chemical entity can include a cholinesterase inhibitor. More particularly, the cholinesterase inhibitor can be selected from the group consisting of donepezil, galantamine, rivastigmine, huperzine A, fasciculin-2, and derivatives thereof.

If donepezil is selected as the ligand 52, the complex rhAChE crystals 60 are characterized with space group P3,21 and have unit cell parameters a=105.15±2 Å, b=105.15±2 Å, c=322.98±2 Å, α=90°, β=90°, and γ=120°. More particularly, in one embodiment, the complex rhAChE crystals 60 have atomic coordinates as deposited with the Protein Data Bank under PDB ID Code 4EY7.

If galantamine, such as 30(-)galamine is selected as the ligand 52, the complex rhAChE crystals 60 are characterized with space group P3,21 and have unit cell parameters a=104.98±2 Å, b=104.98±2 Å, c=323.40±2 Å, α=90°, β=90°, and γ=120°. More particularly, in one embodiment, the crystalline composition has atomic coordinates as deposited with the Protein Data Bank under PDB ID Code 4EY6.

If huperzine, such as 5(-)-huperzine is selected as the ligand 52, the complex rhAChE crystals 60 are characterized with space group P3,21 and has unit cell parameters a=105.22±2 Å, b=105.22±2 Å, c=323.29±2 Å, α=90°, β=90°, and γ=120°. More particularly, in one embodiment, the crystalline composition has atomic coordinates as deposited with the Protein Data Bank under PDB ID Code 4EY5.

If fasciculin-2 is selected as the ligand 52, the complex rhAChE crystals 60 are characterized with space group R32 and have unit cell parameters a=151.70±2 Å, b=151.70±2 Å, c=247.86±2 Å, α=90°, β=90°, and γ=120°. More particularly, in one embodiment, the crystalline composition has atomic coordinates as deposited with the Protein Data Bank under PDB ID 15 Code 4EY8.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method of creating crystals of recombinant human acetylcholinesterase, comprising the steps of:

isolating a first polynucleotide encoding human acetylcholinesterase, wherein said first polynucleotide comprises a nucleotide sequence that has an initiation codon that begins said first polynucleotide, and a stop codon that ends said first polynucleotide, wherein said first polynucleotide includes a 32nd codon and a 33rd codon as counted from said initiation codon;

inserting a second polynucleotide encoding an octahistidine tag into said first polynucleotide sequence between said 32nd codon and said 33rd codon, therein forming a recombinant human cholinesterase construct;

amplifying said recombinant human cholinesterase construct;

transfecting cells on a growth medium with said recombinant human cholinesterase construct to create a colony of cells, wherein said colony of cells secrete an octahistidine-tagged recombinant human cholinesterase polypeptide into said growth medium;

separating said octahistidine-tagged recombinant human cholinesterase polypeptide from said growth medium to form a concentrate;

cleaving said octahistidine-tagged recombinant human cholinesterase polypeptide and removing said octahistidine tag from said concentrate;

exchanging said concentrate into a buffer to create a buffered concentrate; and growing crystals of the recombinant human cholinesterase polypeptide with said buffered concentrate using sitting drop vapor diffusion.

2. The method according to claim 1, wherein said human acetylcholinesterase encoded by the first polynucleotide has 574 amino acids.

3. The method according to claim 1, wherein said second polynucleotide encodes the protease recognition sequence of SEQ ID NO: 2 following the octahistidine tag.

4. The method according to claim 1, wherein amplifying said recombinant human cholinesterase polynucleotide includes amplification by polymerase chain reaction.

5. The method according to claim 4, wherein amplifying said recombinant human cholinesterase polynucleotide further includes cloning said recombinant human cholinesterase construct.

6. The method according to claim 1, wherein cleaving said octahistidine-tagged recombinant human cholinesterase includes cleaving said octahistidine-tagged recombinant human cholinesterase with a his-TEV protease.

7. The method according to claim 1, further including the step of purifying said buffered concentrate.

8. The method according to claim 1, wherein said buffer includes 4-(2-hydroxyethyl)piperazine-1-ethanesulfonic acid, NaCl, and imidazole.

9. The method according to claim 1, wherein growing crystals with said buffered concentrate includes using sitting drop vapor diffusion with a crystallization buffer.

10. The method according to claim 9, wherein said crystallization buffer includes polyethylene glycol and potassium nitrate.

11. The method according to claim 9, further including the step of mixing a ligand into said buffered concentrate.

12. The method according to claim 1, further including the step of soaking said crystals in a solution containing a ligand.

\* \* \* \* \*